United States Patent [19]

Studt et al.

[11] Patent Number: 4,496,573
[45] Date of Patent: Jan. 29, 1985

[54] 1-PYRIDYLMETHYL-3-ACYL GUANIDINES

[75] Inventors: William L. Studt, Harleysville; Harry K. Zimmerman, Kintnersville, both of Pa.

[73] Assignee: William H. Rorer, Inc., Fort Washington, Pa.

[21] Appl. No.: 410,959

[22] Filed: Aug. 24, 1982

[51] Int. Cl.³ .................... C07D 213/53; A61K 31/44
[52] U.S. Cl. .................................... 514/344; 546/332; 546/306; 514/345; 514/350; 514/352; 514/354
[58] Field of Search ................. 546/332, 306; 424/263

[56] References Cited

U.S. PATENT DOCUMENTS 3,914,306 10/1975 Douglas et al. ............... 564/220
4,287,346 9/1981 Tanaka et al. .................. 546/280

FOREIGN PATENT DOCUMENTS 00163 4/1982 European Pat. Off. .
1461806 1/1977 United Kingdom .............. 546/331

OTHER PUBLICATIONS

Nafissi–Varchei et al., CA., 97:72118v.
Peterson et al., CA., 89:99710d.
Douglas et al., CA., 98:160594 and 160595.
Studt et al., CA. 98:185594m.

Primary Examiner—Jane T. Fan
Attorney, Agent, or Firm—James A. Nicholson; Alexis Barron; Martin F. Savitzky

[57] ABSTRACT

1-Acyl-3-pyridyl guanidine and 1-acyl-3-pyridylalkyl guanidine compounds, methods for the treatment of blood pressure disorders, including hypertension, in humans and other mammals.

9 Claims, No Drawings

1-PYRIDYLMETHYL-3-ACYL GUANIDINES

FIELD OF THE INVENTION

This invention relates to 1-acyl-3-pyridyl guanidine and 1-acyl-3-pyridylalkyl guanidines, pharmaceutical compositions including said compounds and methods for lowering blood pressure in humans and other mammals and, in particular, methods for the treatment of hypertension.

BACKGROUND OF THE INVENTION

The pharmaceutical compositions which have been used as antihypertensive agents have included the thiazides, reserpine, hydralazine, α-methyldopa, guanethidine, guanadine, guanachlor and guanoxan among others. These compounds, however, while being effective, produce undesirable side effects such as electrolyte imbalance and orthostatic hypertension, and can adversely effect gastric secretory and spasmolytic functioning.

In U.S. Pat. No. 3,914,306 to Douglas and Diamond, 1-acyl-3-phenylguanidines are disclosed as effective antihypertensive agents possessing a minimum of side effects. However, the toxic dose of acyl phenylguanidines is relatively low and their dose response curve is such that their use as antihypertensive agents must be closely monitored.

Related pyridyl compounds have not been reported as possessing cardiovascular activity. For example, in British Pat. No. 1,461,806, 1-pyridylmethyl thioureas, substituted in the 3-position by alkyl, amino, phenyl, silyl, or acyl were reported as antiulcer and antisecretory agents. In PCT Application PCT/EP81/00163, 1-N-carboalkoxy-1-N'-substituted-3-pyridylguanidines have been reported to be useful as antihelminthics.

The present invention relates to novel 1-acyl-3-pyridylguanidines which exhibit antihypertensive activity and which are therapeutically useful in view of their low toxicity and dose response properties.

SUMMARY OF THE INVENTION

This invention relates to a class of acyl pyridyl and pyridyl-alkyl guanidine compounds according to Formula I.

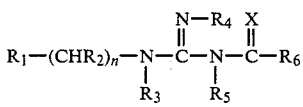

wherein:
X is O or S;
n is 0 or 1;
$R_2$, $R_3$, $R_4$ and $R_5$ are each independently H or alkyl;
$R_6$ is alkyl, cycloalkyl, alkenyl, alkynyl or aralkyl;
$R_1$ is pyridyl or pyridyl having 1 to 4 ring substituents selected from the group consisting of halogen, lower alkyl, lower alkenyl, aryl, lower alkynyl, aralkyl, nitro, cyano, sulfonyl, hydroxyl, carboxyl, lower alkanoyl, lower alkoxy, aryl lower alkoxy, halo lower alkoxy, amido, amino, lower alkyl acyloxy, alkylamino, lower alkoxyamino, and aralkoxyamino; and the N-oxide thereof; or an acid addition salt thereof.

Compounds of Formula I possess pharmaceutical activity, including cardiovascular activity such as blood pressure lowering activity, and are useful in methods of treating blood pressure disorders, such as hypertension, in humans and other animals.

DETAILED DESCRIPTION OF THE INVENTION

Compounds of the invention which are preferred are 1-acyl-3-pyridyl-or 1-acyl, 3-pyridylalkyl guanidines according to Formula I wherein $R_1$ is 2-,3-, or 4-pyridyl or substituted 2-,3, or 4-pyridyl as shown below in Furmulae II, III and IV.

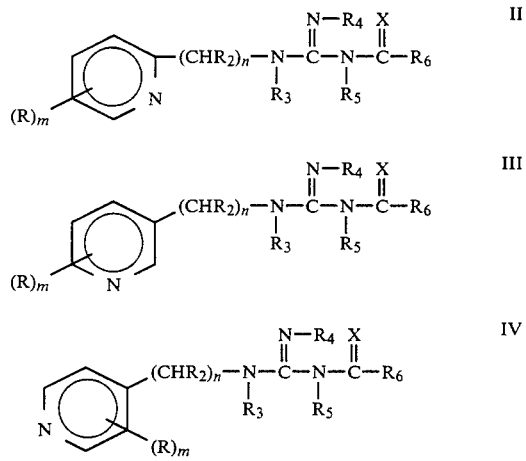

wherein:
X is O or S;
n is 0 or 1;
$R_2$, $R_3$, $R_4$ and $R_5$ are each independently H or alkyl;
$R_6$ is alkyl, cycloalkyl, alkenyl, alkynyl or aralkyl;
R is a ring substituent selected from the group consisting of halogen, lower alkyl, lower alkenyl, aryl, lower alkynyl, aralkyl, nitro, cyano, sulfonyl, hydroxyl, carboxyl, lower alkanoyl, lower alkoxy, aryl lower alkoxy, halo lower alkoxy, amido, amino, lower alkyl acyloxy, alkylamino, lower alkoxyamino, and aralkoxyamino; and m is 0, 1, 2, 3 or 4.

It should be understood that when m is greater than 1, then R may be the same or a different substituent group.

A preferred class of compounds of this invention are compounds according to Formulae II to IV or an acid addition salt thereof wherein:

$R_2$, $R_3$, $R_4$ and $R_5$ are H.

A most preferred class of compounds are those wherein:

$R_6$ is alkyl or cycloalkyl, and, preferably, lower alkyl or cycloalkyl.

A class of compounds of particular interest are compounds according to Formula II, III or IV wherein the pyridyl group is substituted by lower alkyl, halo, halo loweralkyl, lower alkoxy, amino, cyano and lower alkylacyloxy.

As employed above and throughout the disclosure, the following terms, unless otherwise indicated, shall be understood to have the following meanings:

"Alkyl" means a saturated aliphatic hydrocarbon which may be either straight- or branched-chain. Preferred are lower alkyl groups which have up to about 6 carbon atoms, including methyl, ethyl and structural isomers of propyl, butyl, pentyl, and hexyl. "Cycloalkyl" means a saturated cyclic hydrocarbon, preferably having about 3 to about 6 carbon atoms, which may also be substituted with a lower alkyl group.

The term "halo" and "halogen" include all four halogens, namely, fluorine, chlorine, bromine and iodine. The halo alkyls, halophenyl and halo-substituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of a lower alkanoic acid such as acetoxy, propionoxy, and the like.

"Lower alkanoyl" means the acyl radical or a lower alkanoic acid, including acetyl, propionyl, butyryl, valeryl, and stearoyl.

"Lower alkoxy" means the oxy radical of a lower alkyl group, such as methoxy, ethoxy, n-propoxy and i-propoxy.

"Aryl" means a radical of an aromatic group. The preferred aromatic groups are phenyl and substituted phenyl.

"Substituted phenyl" means a phenyl group in which one or more of the hydrogens has been replaced by the same or different substituents including halo, lower alkyl, halo lower alkyl, nitro, amino, acylamino, hydroxy, lower alkoxy, aryl lower alkoxy, acyloxy, cyano, halo lower alkoxy or lower alkyl sulfonyl.

"Aralkyl" means lower alkyl in which one or more hydrogens is substituted by aryl (preferably phenyl or substituted phenyl). Preferred groups are benzyl and phenethyl.

"Alkenyl" means an unsaturated aliphatic hydrocarbon which may include straight or branched chains. Preferred are lower alkenyl groups which have up to about 6 carbon atoms and may be vinyl and any structural and geometric isomers of propenyl, butenyl, pentenyl, and hexenyl.

"Alkynyl" means an unsaturated aliphatic hydrocarbon containing one or more triple bonds. Preferred are lower alkynyl groups which contain up to about 6 carbon atoms and include ethynyl, propynyl, butynyl, pentynyl, and hexynyl.

"Sulfonyl" means a radical of the formula

wherein R is halo, lower alkyl or amino.

"Aryloxy" means the oxy radical of an aromatic group such as phenoxy.

The compounds of this invention may be readily converted to their nontoxic acid addition salts by customary methods in the art. The nontoxic salts of this invention are those salts the acid component of which is pharmacologically acceptable in the intended dosages. Such salts would include those prepared from inorganic acids, and organic acids, such as, higher fatty acids, high molecular weight acids, etc. Exemplary acids include hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

It is well known in the pharmacological arts that nontoxic acid addition salts of pharmacologically active amine compounds do not differ in activities from their free base. The salts merely provide a convenient solubility factor. Other salts, for example, quarternary ammonium salts, are prepared by known methods for quarternizing organic nitrogen compounds.

The compounds of this invention may be prepared by the following general synthesis.

Acylation of a pyridyl-, or pyridylalkyl-, guanidine free base with an acid halide, for example propionyl chloride, results in an acyl pyridyl guanidine. The reaction can be carried out in a polar media such as acetone.

Alternatively, the pyridyl- or pyridylalkyl guanidine free base can be treated with an ester, for example, ethyl acetate, to effect an amide-ester interchange and result in the acylpyridyl-, or acylpyridylalkyl-1 quanidine. Preferred reactions comprise heating the reactants at constant volume and elevated temperatures, for example at 100° C. for one hour to several days.

The pyridyl and pyridylalkyl guanidine free bases are obtained by treatment of the corresponding pyridyl and pyridylalkyl guanidine acid salts with a metal hydroxide or alkoxide solution.

The pyridyl- or pyridylalkyl-guanidine starting materials may be prepared by condensation of cyanamide and a pyridyl- or pyridylalkyl amine.

The reaction is preferably carried out on the amino salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The most preferred solvent is a mildly acidic solvent which is non-nucleophilic such as phenol, cresol, xylenol, etc. The reaction should also be carried out at a temperature which is high enough so that condensation takes place readily, but not sufficient to decompose the guanidine formed. The reaction temperature can vary from room temperature to about 250° C. although it is preferable to run the reaction at temperatures from about 50° C. to 150° C. The guanidine salt which is formed can be converted to the free base with a metal hydroxide or alkoxide solution. The isolation of the desired guanidine can be carried out by any method known in the art.

The starting materials may also be prepared by condensing the desired amino heterocycle with an isothiourea or an isothiouronium salt.

The starting pyridyl primary amines are either known, or may be prepared by known techniques. Thus, chlorination or bromination of a primary or secondary pyridyl or pyridylalkyl substituted amine may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (ClI).

Alkylation may be carried out on an amine using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

A chloro, bromo or iodo compound may also be reacted with trifluoromethyliodide and copper powder at about 150° C. in dimethylformamide to obtain a trifluoromethyl compound (Tetrahedron Letters: 47, 4095 (1959)).

A halo compound may also be reacted with cuprous methanesulfinate in quinoline at about 150° C. to obtain a methylsulfonyl compound.

When it is desired that the final product contain a hydroxy substituted pyridyl group, it is preferred that the starting heterocyclic amine contain the corresponding acyloxy or aralkyloxy groups. These may be prepared in the usual fashion by acylating the starting hydroxy pyridyl compound with acyl halide or anhydride in the presence of a tertiary amine or aralkylating with an aralkyl halide or sulfate. Of course the amine function would be protected in the customary manner. Hydrogenolysis of the aralkyl group to the desired hydroxy compound may then take place after the formation of the Acylguanidine. This may be accomplished with a metal catalyst (Pd/C. Pt etc.) in a polar medium (ethanol, THF, etc.) for example, sodium in liquid ammonia. Thus, for example, the 4-hydroxy-2-pyridyl acylguanidine compound may be prepared from the corresponding 4-benzyloxy-2-pyridyl compound. The hydroxy compounds may also be prepared by selective hydrolysis of the acyl or aralkoxy compounds with acid.

When an alkyl group is desired in the $R_3$, $R_4$, or $R_5$ positions according to Formula I, the reaction sequence described above may be modified accordingly. Exemplary synthetic routes for the pyridyl guanidines and disclosed in applicant's copending PCT Application, Ser. No. PCT/US81/01146, filed on Aug. 24, 1981, and assigned to the assignee of the present application, the disclosure of which is incorporated by reference.

When it is desired that the final product contain an N- or S-oxide of the group $R_1$, starting materials containing this function may be used or the final products may be oxidized using a peroxide, for example, an organic peracid, such as m-chloroperbenzoic acid.

Reactions may also be carried out at other stages of synthesis depending on the substituents present and the substituents desired and various combinations of the foregoing reactions will be determined by one skilled in the art in order that the desired product results. Thus, a pyridylguanidine or 1-acyl-3-pyridylguanidine may be halogenated or nitrated as above, etc.

The following examples illustrate the preparation of the 1-acyl-3-pyridylguanidines of this invention and are not to be construed as a limitation thereof.

EXAMPLE 1

PREPARATION OF 1-ACETYL-3-(2-PYRIDYLMETHYL) GUANIDINE

Step 1 1-(2-Pyridylmethyl) Guanidine Sulfate

2-Aminomethylpyridine (54.07 g) is added to a vigorously stirred solution of 2-methyl-2-thiopseudouronium sulfate (69.60 g) in 200 ml of $H_2O$. The stirred mixture is carefully warmed while being flushed with a continuous stream of $N_2$. Alkaline $KMnO_4$ is used to scavenge for evolved methyl mercaptan. The mixture is stirred at 65° C. over the weekend resulting in a bright yellow solution which is heated to boiling. After refluxing for 30 minutes the solution is filtered while hot and evaporated to dryness under reduced pressure. The residue is a brilliant green crystalline solid which is taken up in hot aqueous methanol. Upon cooling, crystals separate and the solid is collected and dried in vacuo yielding 65.6 g of crystals, MP 206°–207° C. The crystalline solid is taken up in boiling water; a portion of Darco G-60 is added and the mixture filtered. The filtrate is concentrated and cooled. The crystalline precipitate is collected, washed with methanol and dried, yielding 8.6 g of a white crystalline product, MP 208°–209° C. which is determined to be the desired 1-(2-pyridylmethyl) guanidine sulfate.

Step 2 1-Acetyl-3-(2-Pyridylmethyl) Guanidine 19.92 g of 1-(2-pyridylmethyl) guanidine sulfate and 5.94 g of sodium methoxide are added to 100 ml of methanol. The mixture is stirred for 2½ hrs. at RT and filtered. The resulting solid is washed with methanol, and the solvent evaporated in vacuo, yielding a red solid. Absolute ethanol is added to the red solid in two stages and the resulting mixture is filtered. The filtered solid is washed with absolute ethanol and the solvent evaporated in vacuo yielding the guanidine as a solid. The guanidine is dissolved in 150 ml of boiling ethyl acetate and the solution separated from any residue and concentrated under $N_2$. The concentrated solution is heated in a sealed stainless steel bomb at 100° C. for one day. The reaction mixture is cooled, diluted with ethyl acetate containing a trace of methanol, heated, concentrated and cooled, resulting in the formation of a precipitate. The precipitate is washed with ethyl acetate and dried in vacuo yielding the desired acetyl guanidine as a white powder, M.P. 148°–150° C.

EXAMPLE 2

PREPARATION OF 1-PROPIONYL-1-(2-PYRIDYLMETHYL)GUANIDINE SUCCINATE

A suspension of 8.00 g of 50% aqueous NaOH, 19.92 g of 2-pyridylmethyl guanidine sulfate and 100 ml of acetone is stirred for 3½ hrs. at RT. 8 g of anhydrous sodium sulfate is added to the suspension and the reaction mixture stirred for 2 hrs. The reaction mixture is treated dropwise with a solution of 4.35 ml propionyl chloride in 100 ml acetone, stirred overnight at RT and filtered. The filtrate is evaporated in vacuo to a tan oil. The oil is dissolved in 100 ml of methylene chloride and the resulting solution is washed with $H_2O$. The aqueous layer is extracted with methylene chloride. The combined organic extract is dried over sodium sulfate, filtered and evaporated in vacuo (0.1 mm) to an oil. The residue is dissolved in hot 2-propanol, 3.32 g succinic acid added, and the resulting mixture heated until a solid begins to form. The solid is collected, washed with 2-propanol and dried in vacuo to yield the desired guanidine succinate as a white powder, M.P. 168°–170° C.

EXAMPLE 3

PREPARATION OF 1-CYCLOHEXYLCARBONYL-3-(2-PYRIDYL-METHYL) GUANIDINE

A mixture of 8.00 g of 50% aqueous NaOH, 19.92 g of 2-pyridylmethyl guanidine sulfate, and 100 ml of acetone is stirred overnight at RT. Anhydrous sodium sulfate (8 g) is added to the mixture and stirring continued for 5 hr. A solution of 7.33 g of cyclohexyl carbonyl chloride in 100 ml of acetone is added dropwise to the stirred mixture and the reaction mixture allowed to stand over the weekend. The solvent is evaporated in vacuo and the residue partitioned between methylene chloride and H$_2$O. The aqueous phase is separated and extracted with methylene chloride. The combined organic extract is dried over sodium sulfate, filtered and the filtrate evaporated in vacuo, yielding the guanidine as a solid.

The guanidine compounds of this invention possess blood-pressure-lowering activity and are useful as antihypertensive agents.

Various tests in animals have been carried out to show the ability of the compounds of this invention to exhibit reactions that can be correlated with activity in humans. These tests involve such factors as their blood-pressure-lowering effect and determination of their toxicity. It has been found that the compounds of this invention, when tested in the above situation, show a marked activity.

Determination of Antihypertensive Activity

A description of the test protocol used in the determination of the antihypertensive activity of the compounds of this invention follows:

(a) Male TAC spontaneously hypertensive rats (SHR's), eleven weeks old, weighing 200–220 g, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury monometer is placed on one arm of the glass "T" tube. The known pressure head in the tail cuff is synchronized with the recorder output so that 1 mm pen deflection = 5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed on the rat's tail and the rubber bulb of the pneumatic tail cuff transducer is taped securely to the dorsal surface of the tail. When the rat's pulse reaches maximum amplitude and is unwavering, the cuff is inflated and the air slowly released. A reading of systolic blood pressure is read at the point of the chart when the first deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of twenty rats received the test compounds at doses of about 25 mg/kg per oz.

A fourth group of twenty control rats received distilled water. Statistical comparisons of systolic pressure (four hours after the first dose and sixteen hours after the second dose) are made on a daily basis using the Student t test for dependent variables (see, E. Lord, *Biometrika*, 34, 56 (1947), with the predose observations serving as baseline values for each rat.

This testing method is known to correlate well with antihypertensive activity in humans and is a standard test used to determine antihypertensive properties. In view of the results of this test, the pyridyl and pyridylalkylacylguanidines of this invention are blood pressure lowering agents and can be considered to be active antihypertensive agents. A preferred antihypertensive compound of this invention is 1-acetyl-3-(2-pyridylmethyl) guanidine.

For use in the treatment of cardiovascular disorders, the guanidines of this invention can be normally administered orally, parenterally or rectally. Orally they may be administered as tablets, aqueous or oily suspensions, dispersible powders or granules, emulsions, hard or soft capsules, or syrups or elixirs. Parenterally they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more inert carrier agents selected from the group consisting of sweetening agents, flavoring agents, coloring agents, preserving agents and the like, in order to provide a pharmaceutically elegant and palatable preparation.

The dosage regimen in carrying out the methods of this invention is that which ensures maximum therapeutic response until improvement is obtained, and thereafter the minimum effective level which gives relief. Thus, in general, the dosages are those that are therapeutically effective in the alleviation of hypertensive disorders. The therapeutically effective doses correspond to those dosage amounts found effective in tests using animal models which are known to correlate to human activity. In general, it is expected that doses between about 0.05 mg/kg and about 50 mg/kg (preferably in the range of about 0.5 mg/kg to about 20 mg/kg, will be sufficient to produce the desired therapeutic effect, bearing in mind, of course, that in selecting the appropriate dosage in any specific case, consideration must be given to the patient's weight, general health, age, the severity of the disorder, and other factors which may influence response to the drug. The composition containing the effective dose may be administered from about one to about four times a day.

We claim:

1. A compound of the formula

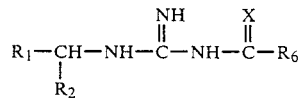

wherein:

X is O or S;

R₂ is H or lower alkyl;

R₆ is lower alkyl, cycloalkyl of 3 to 6 carbon atoms, lower alkenyl, lower alkynyl, phenyl lower alkyl or substituted phenyl lower alkyl;

R₁ is pyridyl or pyridyl having 1 to 4 ring substituents selected from the group consisting of halogen, lower alkyl, lower alkenyl, phenyl, lower alkynyl, phenyl lower alkyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkoxyamino;

and the N-oxide thereof;

wherein substituted phenyl means a phenyl group in which one or more hydrogens is replaced by halo, lower alkyl, halo lower alkyl, nitro, amino, lower alkanoylamino, hydroxy, lower alkoxy, phenyl lower alkoxy, lower alkanoyloxy, cyano, halo lower alkoxy or lower alkyl sulfonyl;

or a pharmaceutically acceptable acid addition salt thereof.

2. A compound of the formula

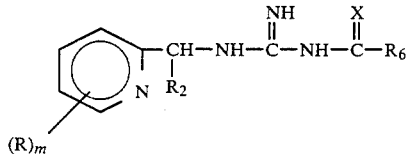

wherein:

X is O or S;

m is 0, 1, 2, 3 or 4;

R₂ is H or lower alkyl;

R₆ is lower alkyl, cycloalkyl of 3 to 6 carbon atoms, lower alkenyl, lower alkynyl or phenyl lower alkyl;

R is a ring substituent selected from the group consisting of halogen, lower alkyl, lower alkenyl, phenyl, lower alkynyl, phenyl lower alkyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkoxyamino;

and the N-oxide thereof;

or a pharmaceutically acceptable acid addition salt thereof.

3. A compound of the formula

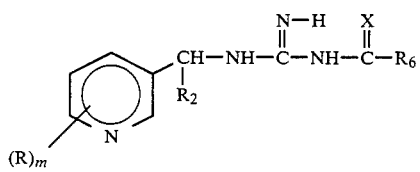

wherein:

X is O or S;

m is 0, 1, 2, 3 or 4;

R₂ is H or lower alkyl;

R₆ is lower alkyl, cycloalkyl of 3 to 6 carbon atoms, lower alkenyl, lower alkynyl or phenyl lower alkyl;

R is a ring substituent selected from the group consisting of halogen, lower alkyl, lower alkenyl, phenyl, lower alkynyl, phenyl lower alkyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkoxyamino;

and the N-oxide thereof;

or a pharmaceutically acceptable acid addition salt thereof.

4. A compound of the formula

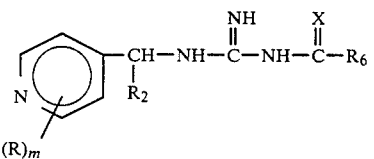

wherein:

X is O or S;

m is 0, 1, 2, 3 or 4;

R₂ is H or lower alkyl;

R₆ is lower alkyl, cycloalkyl of 3 to 6 carbon atoms, lower alkenyl, lower alkynyl or phenyl lower alkyl;

R is a ring substituent selected from the group consisting of halogen, lower alkyl, lower alkenyl, phenyl, lower alkynyl, phenyl lower alkyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkylamino;

and the N-oxide thereof;

or a pharmaceutically acceptable acid addition salt thereof.

5. A compound according to claim 1, 2, 3 or 4 wherein:

R₆ is lower alkyl or cycloalkyl of 3 to 6 carbon atoms.

6. 1-propionyl-3-(2-pyridylmethyl) guanidine or a pharmaceutically acceptable acid addition salt thereof.

7. 1-acetyl-3-(2-pyridylmethyl) guanidine or a pharmaceutically acceptable acid addition salt thereof.

8. 1-Cyclohexylcarbonyl-3-(2-pyridylmethyl) guanidine or a pharmaceutically acceptable acid addition salt thereof.

9. A method for lowering blood pressure in humans and other mammals comprising administering to a patient in need of lower blood pressure an effective blood pressure lowering amount of a compound according to claim 1.

* * * * *